United States Patent

Findlater

Patent Number: 5,810,003
Date of Patent: Sep. 22, 1998

[54] INFANT DECONGESTER

[76] Inventor: Barrington M. Findlater, 6102 4th Manor West, Palatka, Fla. 32177

[21] Appl. No.: 811,317

[22] Filed: Mar. 4, 1997

[51] Int. Cl.[6] .................................................. A61J 7/00
[52] U.S. Cl. .............................. 128/203.12; 128/202.15; 128/200.14; 215/11.1
[58] Field of Search ..................... 128/203.12, 202.15, 128/200.14, 202.17, 204.13; 604/77, 78; 606/236; 215/11.1

[56] References Cited

U.S. PATENT DOCUMENTS

| | | | |
|---|---|---|---|
| 3,565,071 | 2/1971 | Cobb et al. | 128/204.13 |
| 4,669,461 | 6/1987 | Battaglia et al. | 128/202.15 |
| 4,821,895 | 4/1989 | Roskilly | 215/11.1 |
| 4,915,242 | 4/1990 | Marte | 215/11.1 |
| 5,316,160 | 5/1994 | Cautereels | 215/11.1 |
| 5,386,825 | 2/1995 | Bates | 128/204.13 |
| 5,542,922 | 8/1996 | Petterson et al. | 215/11.1 |

*Primary Examiner*—Aaron J. Lewis
*Assistant Examiner*—V. Srivastava

[57] ABSTRACT

A decongesting device for administering medicinal vapors directly to the nostrils of infants. The infant decongester comprises a ring of medicated material 16 encased in a perforated hollow flange 18 and cover 20. Said ring is made of a material such that it can absorb medicines that emit decongesting vapors. Said flange and cover are made of a sufficiently rigid material and permanently sealed so as to isolate said ring from infant. The infant decongester is fitted around the neck 22 of a feeding container 26 and then held securely in place by a cap and nipple assembly 28.

2 Claims, 2 Drawing Sheets

5,810,003

INFANT DECONGESTER

BACKGROUND—FIELD OF INVENTION

This invention concerns a device that delivers decongesting vapors to the nostrils of infants.

Historically, infants with cold-related ailments such as coughing swollen or clogged nasal passages and congestion have been treated internally with syrups and externally with body rubs such as "VICKS® decongester, manufactured by Procter & Gamble of Cincinnati."

Subsequently, severely congested infants have forced parents and care-givers into some creative methods of getting the decongesting medication as close as possible to the nostrils of infants.

Cold syrups are rarely adminstered to infants in the correct dosage and quite often do not work to relieve congestion or do not work immediately.

When adults encounter the need for immediate relief of nasal congestion, devices such "VICKS® INHALER, manufactured by Procter & Gamble of Cincinnati", provide the required relief.

OBJECTS AND ADVANTAGES

The objects of the present invention are:

(a) to provide a simple device that delivers medication directly to the nostrils of infants.

(b) to provide a device of the aforesaid nature which will operate at feeding time and at nap time.

Further objects and advantages are to eliminate "creative" and unsafe methods of providing relief to infants such as smearing vapor emitting medication on to the upper lip or inside the nasal passages. Such home remedies are universal and the unavoidable discomfort or occasional injury to eyes, skin and nostrils are common.

Infants suffer the most distress due to "stuffy noses" at feeding time or at nap time.

DRAWING FIGURES

Figure 1B:
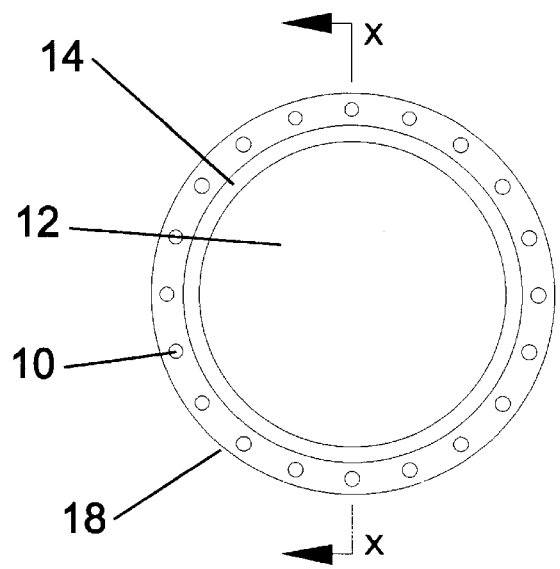
FIG. 1B shows a top view of the device of FIG. 1A.

REFERENCE NUMERALS IN DRAWINGS 10 small holes in surface of flange
12 large hole in center of flange
14 tapered section of flange
16 ring of absorbing material
18 hollow flange
20 cover
22 neck
24 shoulder
26 feeding bottle
28 cap and nipple assembly

SUMMARY

In accordance with the present invention, an infant decongester comprises a vapor emitting core element encased in a holder which attaches to a feeding container, said container's cover assembly or a pacifier.

DESCRIPTION—FIGS.1A,1B,1C,2

Figure 1C:
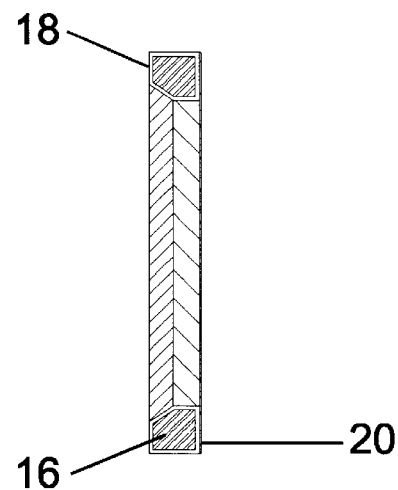
FIG. 1C shows a section taken on line X—X in FIG. 1B
Figure 1A:
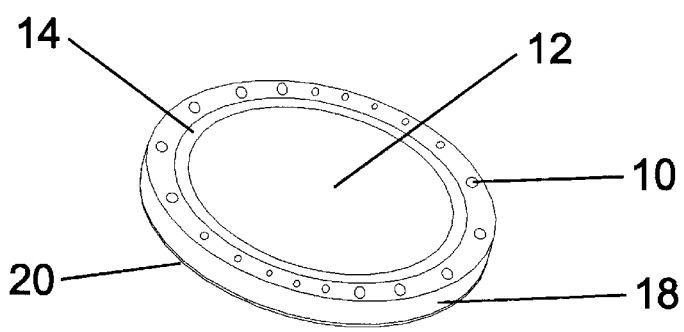
FIG. 1A shows a perspective of a preffered embodiment of an infant decongester.
Figure 2:
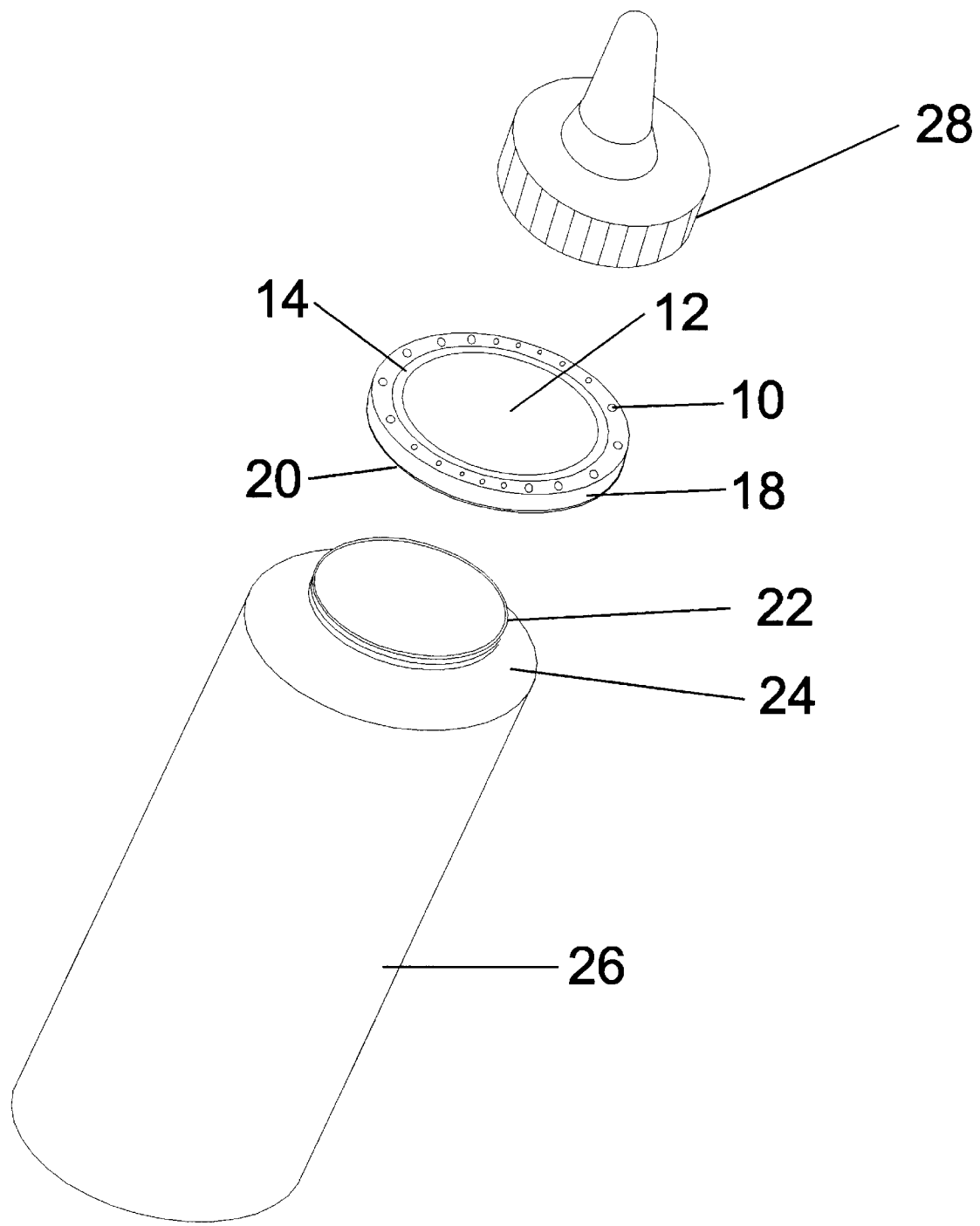
FIG. 2 shows a perspective view of one application of the device of FIG. 1A.

A typical embodiment of the infant decongester of the present invention is illustrated in FIG. 1A (perspective view), FIG. 1B (top view ) and FIG. 1C (cross-sectional view). The infant decongester has a ring of material 16 which can absorb vapor emitting compounds such as camphor, menthol and/or eucalyptus oil and emit decongesting vapors. In the preffered embodiment the ring is cotton. However the ring can consist of any other material that will absorb said vapor emitting compounds such as felt, paper products, various impregnated or laminated fibrous material etc.

The ring 16 is encased in a holder which consists of an open end hollow flange 18 and cover 20. In the preferred embodiment, the flange 18 and cover 20 are made of sufficient rigidity to meet current safety standards. The cover 20 is permanently affixed to the open end of the flange 18 by virtue of adhesive upon the contact surfaces of cover 20 and flange 18. The flange 18 has a circular hole 12 in it that is of such a diameter to fit over a standard, existing feeding bottle 26. The surface 14 of the flange 18 (adjacent to the hole 12) is tapered so as to provide a snug fit under a cap and nipple assembly 28. The surface of flange 18 has holes 10 to enable the delivery of vapors.

OPERATION—FIG. 2

The manner of using the infant decongester of the present invention (preferred embodiment) is as follows. One prepares a feeding bottle 26 for infant. Next, one slips said decongester over neck 22 of said bottle 26 such that said decongester rests on shoulder 24 of said bottle 26. Next one screws cap and nipple assembly 28 on to neck 22 to close bottle 26 and secure said decongester.

SUMMARY, RAMIFICATIONS, AND SCOPE

Thus the reader will see that the decongester of the current invention provides a simple device that can easily be used and eliminates the need for "creative methods" of delivering immediate relief to infants at the most distressing times.

While my above description contains many specificities, these should not be construed as limitations on the scope of the invention but rather as an exemplification of one preferred embodiment thereof. Many other variations are possible. For example, the decongester can have other shapes such as cubical, spherical, cylindrical etc; the method of connection to a feeding container can be such as to wedge said decongester to outside of container or to the outside of cap and nipple assembly; the decongester can be made in two hinge-connected halves that can be fastened around the container etc.

Also the decongester can attached as described above so as to be made a permanent part of a feeding container, cap and nipple assembly or a pacifier.

The ring of absorbing material may not be encased in a holder if safety permits; the ring may be solid etc.

Thus the scope of the invention should be determined by the appended claims and their legal equivalents rather than by the examples given.

I claim:

1. A device that will dispense beneficial vapors to infants comprising:

(a) a predetermined core element means, that will emit beneficial vapors, and (b) a holder surrounding and encasing said core element means with a plurality of holes in said holder so as to enable said core element means to dispense beneficial vapors, whereby said holder protects infant from ingesting said core element and provides a means of attachment of said holder to infant feeding containers, cover and nipple assembly or infant pacifiers.

2. The device of claim 1 wherein said device is not a separate detachable entity but is incorporated to and made a permanent fixed, undetachable component of a feeding container, cover and nipple assembly or pacifier.

* * * * *